United States Patent
Noguchi

(10) Patent No.: US 7,018,464 B2
(45) Date of Patent: Mar. 28, 2006

(54) BODY PIGMENT AND PROCESS FOR PREPARING THE SAME

(75) Inventor: Tamio Noguchi, Iwaki (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/384,781

(22) Filed: Mar. 11, 2003

(65) Prior Publication Data

US 2004/0011253 A1    Jan. 22, 2004

(30) Foreign Application Priority Data

Mar. 11, 2002    (JP) .............................. 2002-065335

(51) Int. Cl.
| | |
|---|---|
| *C04B 14/00* | (2006.01) |
| *C09D 11/00* | (2006.01) |
| *C01F 11/02* | (2006.01) |
| *A61K 7/32* | (2006.01) |
| *C09K 21/00* | (2006.01) |

(52) U.S. Cl. .................. 106/401; 106/461; 106/463; 106/31.6; 423/635; 423/637; 423/638; 424/65; 424/401; 424/682; 424/692; 252/601

(58) Field of Classification Search ................ 106/401, 106/461, 463; 423/635, 637, 638
See application file for complete search history.

(56) References Cited

U.S. PATENT DOCUMENTS 4,698,379 A * 10/1987 Nakaya et al. .............. 523/513
5,039,509 A *  8/1991 Miyata et al. .............. 423/636
5,240,692 A *  8/1993 Morifuji ..................... 423/431

* cited by examiner

*Primary Examiner*—J. A. Lorengo
*Assistant Examiner*—Patricia L. Hailey
(74) *Attorney, Agent, or Firm*—Millen, White, Zelano, Branigan, P.C.

(57) ABSTRACT

A body pigment with a good skin feel for cosmetics is provided which has an appropriate crumbling property and combines slipping property and adhesiveness without compromising oil absorption. The body pigment is comprised of a metal-containing compound and has a structure in which leaf-shaped flakes are combined and/or intersected.

20 Claims, No Drawings

BODY PIGMENT AND PROCESS FOR PREPARING THE SAME

FIELD OF THE INVENTION

The present invention relates to a body pigment and a process for preparing the same.

BACKGROUND OF THE INVENTION

As the body pigment for cosmetic products, spherical silica and spherical polymers comprised of nylon, polyethylene, and polymethacrylate are known and being used. However, there is still a need for a powder having good slipping property (spreadability) and adhesive property to the skin. Moreover, there is a case in which the body pigment is required to have a function of exhibiting anti-slipping property after exhibiting a certain level of slipping property. And, as a matter of course, the body pigment must be capable of absorbing sebaceous component as its basic prerequisite. In recent years, body pigments intended for improving spreadability have been disclosed such as, for example, agglomerated pigment particles (JP-A-2001-22031S, JP-A-2001-247790, etc.) which are combined with a moisturizer or various organic matters and are given a crumbling property.

However, these body pigments do not have sufficient adhesiveness, though they have a good slipping property to the skin. Also, when considering the uses in all types of cosmetics, their application area may be limited depending on the kinds of the binders because they are a randomly agglomerated body which is previously combined by the bonding action of a moisturizer. Therefore, there is need for a body pigment which has good slipping property and adhesive property and also provides versatility of application without being limited by the type of the binder.

Magnesium hydroxide and basic magnesium carbonate are known as a flame retarding additive (hereinafter referred to 'flame retardant') which is incorporated in a resin component and paper (for example, JP-A-H3-197316, JP-A-H3-197314). Most of these flame retardants make use of the endothermic reaction through which these compounds change into oxides. To maximize the flame retardant effect in the course of these changes, a shape factor of the pigment plays an important role, i.e., a pigment with a large surface area per unit volume is desirable.

A process for preparing magnesium hydroxide is disclosed in which magnesium oxide is added to the slurry of magnesium hydroxide to form spherical or scaly leaf like fine particles through hydration, and then these particles are deposited on the surface of secondary particles of the magnesium hydroxide (JP-A-2001-158617). This process includes generation of secondary particles of magnesium hydroxide and succeeding hydration treatment on the surface of the secondary particles by adding magnesium oxide particles. Thus, this process relates to a highly concentrated surface treatment of water slurry to improve its transport efficiency. In other words, the process is to provide a pigment with a dual structure consisting of a secondary particle at the center and other particles on its surface through a two-step processing. And because of the nonuniform stepped surface structure, the particle lacks smooth slipping property and therefore is not desirable for use in cosmetic body pigments.

Moreover, as an example of readily crumbling soft agglomerated powders, an agglomerated powder, of which the primary particle is coated with solid type organic matter and liquid oil, is disclosed which has both a good slipping property and an anti-slipping property (JP-A-9-31158). In this powder, since the coating material is limited to organic materials and a liquid oil is used therewith, its application to cosmetics may be limited depending on the kind of the liquid oil. Also, this powder is not preferable in that due to the agglomerated particle structure, it has low adhesive property between particles and would be easily exfoliated when used in real cosmetic products.

SUMMARY OF THE INVENTION

It is an object of the present invention to provide a body pigment for cosmetics which has a good skin feel and an appropriate crumbling property, and also combines slipping property and adhesiveness without compromising oil absorption. Upon further study of the specification and appended claims, further objects and advantages of this invention will become apparent to those skilled in the art.

The present invention provides a body pigment with a quite unique structure in which more than two flakes, e.g. leaf-shaped, are combined and/or intersected by adding an aqueous solution of a metal-containing salt and an alkaline aqueous solution or an aqueous solution of magnesium carbonate at the same time into water to produce a metal-containing compound. It was found that at least some of the above mentioned problems can be solved by using this body pigment.

Accordingly, the present invention relates to a body pigment comprising a metal-containing compound, wherein said body pigment has a structure in which more than two, e.g. leaf-shaped, flakes having different orientations are combined and/or intersected.

The present invention further relates to the above described body pigment, wherein said body pigment is preferably substantially spherical. That is, the multiple flakes are combined/intersected such that the general outer shape of such combination/intersection is substantially spherical or an irregular globular shape.

The present invention also relates to the above described body pigment, characterized in that the metal-containing compound is preferably a magnesium compound.

The present invention further relates to the above described body pigment, characterized in that the magnesium compound is preferably selected from the group consisting of magnesium hydroxide, basic magnesium carbonate, and magnesium oxide compounds.

The present invention also relates to the above described body pigment, characterized in that the mean particle diameter of the body pigment is preferably 3 to 80 μm.

The present invention further relates to the above described body pigment, characterized in that the metal-containing compound is preferably either a metal-containing compound predominantly composed of magnesium hydroxide whose oil absorption is not more than 150 (ml 100 g) or a metal-containing compound predominantly composed of basic magnesium carbonate whose oil absorption is 150 to 400 (ml/100 g).

The present invention also relates to the above described body pigment, characterized in that the friction coefficient (MIU value) of the body pigment measured with a KES friction tester is preferably not larger than 0.6.

The present invention also relates to the above described body pigment, characterized in that the compression energy of the body pigment measured with a KES compression tester is preferably 0.1 to 0.7 (gf·cm/cm$^2$).

The present invention also relates to the above described body pigment, characterized in that the compressive resiliency of the body pigment measured with a KES compression tester is preferably 15 to 50%.

The present invention further relates to a process for preparing a body pigment, comprising the steps of dropping simultaneously an aqueous solution of a metal-containing salt and an alkaline aqueous solution or an aqueous solution of carbonate salt into water under stirring to form a precipitate, separating/washing the precipitate thereafter, and drying the same.

The present invention further relates to the above described process for preparing a body pigment, further comprising a step of calcining the precipitate.

The present invention further relates to the above described process for preparing a body pigment, characterized in that the aqueous solution of a metal-containing salt comprises sulfate ions and the ionic concentration ratio of sulfate ion/metal ion is preferably 0.3 to 2.0.

The present invention further relates to a cosmetic material comprising the above described body pigment, wherein the cosmetic material further comprises one or more further ingredients selected from the group consisting of skin protectant, colorant, other body pigments, anti-sunburn agent, antiperspirant, moisturizer, antimicrobial agent/microbicide, skin feeling improver, and oil.

The present invention further relates to a makeup cosmetic material, preferably comprising at least 5% by weight of the above described body pigment.

The present invention further relates to a use of the above described body pigment as a flame retardant.

The present invention further relates to a flame retardant molded product comprising resin or paper and the above described body pigment.

The present invention further relates to a use of the above described body pigment for plastics, paints, coatings, powder coatings, agricultural foils, laser markings, printing or inks.

The body pigment of the present invention is formed of a metal-containing compound having a single form structure in which leaf-shaped flakes are combined or intersected. Since the body pigment of the present invention may have a form of substantially spherical particles, it has good slipping property as well as good crumbling property. Also, when used in a cosmetic material, for example, the pigment provides the cosmetic material having extremely good adhesiveness since, for example, when rubbed into the skin, the particles break into smaller particles and the resulting broken leaf-shaped flakes readily adhere to the skin. Also owing to the structure in which leaf-shaped flakes are combined or intersected, the body pigment has porous characteristics thereby ensuring a good oil absorption property. Moreover, the body pigment of the present invention is formed of a metal-containing compound having a single form structure without containing any binders, and therefore, there is no need for considering effects from other components when adding it to cosmetic materials, and thus it can be used without limitations. Furthermore, according to the process of the present invention, the above described body pigment may be prepared readily and reliably without using other binders in the preparation process as described above.

When the body pigment of the present invention is comprised of a magnesium compound such as magnesium hydroxide, it can be used as a flame retardant material. Although the body pigment has a large surface area due to its leaf-shaped structure, it has good dispersibility owing to its substantially spherical particle structure and therefore can be preferably used for the manufacture of flame retardant resin moldings.

The present invention will be described in more detail below.

The body pigment relating to the present invention is formed of a metal-containing compound which has a single form structure in which leaf-shaped flakes have grown in different orientations.

The metal-containing compound in the present invention includes those comprised of iron, magnesium, aluminum, and others, and more specifically metal hydroxide, basic metal carbonates, metal oxides, etc. can be mentioned as examples.

Especially, metal-containing compounds comprised of magnesium are preferable including magnesium hydroxide, basic magnesium carbonate, and magnesium oxide. Though more details of the process for preparing these compounds are to be described later, for example, when an aqueous solution of magnesium salt and an alkaline aqueous solution are used, magnesium hydroxide is obtained and when an aqueous solution of carbonate is used instead of an alkaline aqueous solution, basic magnesium carbonate is obtained. Also, depending on the conditions of the drying/calcining process, i.e., the higher the temperature and the longer the time, the content of magnesium oxide increases. The expression of "magnesium hydroxide, basic magnesium carbonate, or magnesium oxide" in this specification is intended to include all intermediate conditions (i.e., mixed conditions of hydroxide and oxide, and mixed conditions of basic magnesium carbonate, carbonate, and oxide).

The mean particle size of the body pigment of the present invention is preferably within a range of 3 to 80 μm in view of skin feel such as slipping property and abnormal feel during use. According to the present invention, a particle size of 3 to 40 μm is preferably obtained for magnesium hydroxide, and a particle size of 20 to 80 μm for basic magnesium carbonate.

Within these ranges of particle size, the particle size of the body pigment of the present invention is appropriately selected depending on the embodiment and the application area of the invention.

The cosmetic body pigments used in the present invention preferably have a friction coefficient (MIU) measured with a KES-SE friction tester of not more than 0.6 in view of slipping property. This is an index to represent the slipping property in which a lower figure indicates a better slipping property.

The body pigments obtained by the present invention preferably have a compressive energy of within a range of 0.1 to 0.7 (gf·cm/cm$^2$) when measured with a KES-G5 compression tester. Generally the larger figures of the compression energy indicate larger easiness to compression, and the foregoing range of the compression energy showed good skin feel. The body pigments obtained by the present invention also have a compressive resiliency of 15 to 50% when measured with a KES-G5 compression tester. The larger figures of the compressive resiliency indicate higher recoverability. Therefore smaller figures indicate plastic properties and larger figures indicate elastic properties (recoverability). A body pigment having a compression energy and a compressive resiliency within the above described ranges has an appropriate elasticity and therefore provides both softness and appropriate crumbling property when used as cosmetic material and thus it is preferable.

The metal-containing compounds used in the present invention include a metal-containing compound whose main component is magnesium hydroxide having an oil absorption of not larger than 150 (ml/100 g) or basic magnesium carbonate having an oil absorption of 150 to 400 (ml/100 g). For example, a metal-containing compound dominantly comprised of basic magnesium carbonate is suitable for use in antiperspirants because of its large oil absorbing capacity.

The process for preparing the body pigments of the present invention will be described in more detail below.

The process adopted in the present invention comprises steps of: separately preparing an aqueous solution of a metal-containing salt and an alkaline aqueous solution or an aqueous solution of carbonate salt; dropping the aqueous solutions simultaneously into preheated-preferably above 50° C., more particularly, 70° to 90° C. water under stirring while maintaining its pH at a constant value within a range of 7.5 to 11; and filtering, collecting, washing, drying, and in some cases, calcining the precipitates obtained. In the dropping step, if the aqueous solution of a metal-containing salt and the alkaline aqueous solution or the aqueous solution of carbonate are not dropped simultaneously without adjusting the pH value, the particle shape of the precipitates would become distorted from a spherical shape and also the particle size would become nonuniform, thus this is not preferable.

For example, when preparing a body pigment of the present invention comprised of a magnesium compound, magnesium salt compounds used for preparing an aqueous solution of magnesium salt include magnesium sulfate, magnesium nitrate, magnesium chloride, magnesium acetate, and magnesium oxalate. All of which are used as aqueous solution. Even when using a magnesium salt having a low solubility to water, it can be used by making it water-soluble by using sulfuric acid which acts also as a sulfuric ion source as described later.

To prepare the particle of the pigment of the present invention which has a structure in which leaf-shaped flakes grown in different orientations are combined or intersected each other, sulfuric ion concentration in the preparation process is an important factor and preferably the ion concentration ratio of sulfuric ion/metallic ion (for example, in the case of magnesium, ion concentration ratio of ionized sulfuric ion $((SO_4)^{2-}$/magnesium ion $((Mg)^{2+}))$ is within a range of 0.3 to 2.0. When the ion concentration ratio is less than 0.3, spheroidizing of the particle would not occur especially in the case of magnesium hydroxide. On the contrary, when the ion concentration exceeds 2.0, there would be no significant changes except only an increase in the usage of sulfuric ion source materials and an associated increase of the alkaline component or the carbonate component to be consumed.

In this respect, using magnesium sulfate from the beginning is preferable in that other sulfuric ion resources are not needed in the later processes of the preparation. And when magnesium sulfate is not used as the aqueous solution of magnesium salt, a process of mixing and dissolving various sulfate compounds (hereinafter, referred to as "additional sulfate compounds") into the aqueous solution of magnesium salt in advance can be adopted to make up for the sulfuric ion resource. Moreover, when magnesium sulfate is used, a process of mixing and dissolving additional sulfate compound in advance may also be adopted if the concentration of sulfuric ion is raised higher than the equivalent weight (the ion concentration ratio of sulfuric ion $(SO_4)^{2-}$/magnesium ion $((Mg)^{2+})$ is more than 1 and not more than 2). Examples of the additional sulfate compound are sodium sulfate, potassium sulfate, ammonium sulfate, sulfuric acid, etc. And when using a low solubility magnesium salt as described, a sulfuric acid is preferably used as the additional sulfate compound.

The concentration of the aqueous solution of magnesium salt of the present invention is basically arbitrary as long as the condition of a complete dissolution is satisfied, and generally a concentration of 0.2 to 1.0 mol/liter is adopted. This concentration is suitably determined depending on the equipment, the production scale, and other factors.

In the present invention, the precipitation pH is determined within a range of 7.5 to 11 so that the desired metal-containing compounds can be precipitated.

The alkaline components used for hydrolysis in the present invention include sodium hydroxide, potassium hydroxide, and ammonium hydroxide. To obtain basic magnesium carbonate, carbonate compounds are used including sodium carbonate, potassium carbonate, and ammonium carbonate. All of these are used as an aqueous solution.

The reactions adopted in the present invention are preferably performed under warm water and more preferably at a temperature of not lower than 50° C. in view of the easily forming spherical particles. And in the point of workability, a temperature range of 70 to 90° C. is particularly preferable.

From the thus prepared suspension comprised of magnesium hydroxide or basic magnesium carbonate, precipitates are separated by, for example, filtering or centrifugal separation and isolated water-soluble salts deposited on the precipitates are washed and removed. The following steps include drying and, for some cases, calcining the precipitates. In these steps, as the temperature rises and the residence time increases, the magnesium hydroxide is gradually dehydrated to change to magnesium oxide, and therefore, a mixture containing intermediate products during the change process is obtained. Moreover, in the case of basic magnesium carbonate, it is gradually dehydrated and de-gassed to change to magnesium carbonate and further to magnesium oxide, and therefore a mixture of intermediate products during the change process is obtained.

The drying temperature of the present invention is generally selected within a range of 105° C. to 150° C. The main purpose of the drying step is to remove isolated water and deposited water and the drying time is suitably selected. Depending on the condition of the drying step, a product whose main component is either magnesium hydroxide or basic magnesium carbonate is obtained. Furthermore, in the present invention, the powder obtained by drying is calcined in some cases. By adopting this process, a product with a high content of magnesium oxide as described above is obtained. In contrast, basic magnesium carbonate becomes dehydrated or decomposed at high temperatures generating carbon dioxide gas and changes to magnesium carbonate and further to magnesium oxide Therefore, to retain it as basic magnesium carbonate, it is preferable not to apply the calcining. However, calcining in a temperature/time condition that would not generate decomposed carbon dioxide gas would not be a problem.

When the body pigments in the present invention is used as a flame retardant, it is preferable to perform the drying without calcining to obtain magnesium hydroxide because the retardant utilizes the endothermic reaction during phase transformation from magnesium hydroxide to magnesium oxide. To obtain a product with a high concentration of magnesium oxide, a calcining temperature of not lower than 350° C. is preferable. In this temperature range, as the calcining temperature rises and the calcining time becomes longer, the product changes gradually from a state of high contents of magnesium hydroxide and basic magnesium carbonate to a state of a high magnesium oxide content.

Thus, a body pigment having a mean particle diameter of 3 to 80 μm can be obtained. More specifically, a mean particle diameter of 3 to 40 μm for magnesium hydroxide and 20 to 80 μm for basic magnesium carbonate are obtained. The oil absorption of the body pigments according to the present invention is, for example, not more than 150 (ml/100 g) for magnesium hydroxide and 150 to 400 (ml/100 g) for basic magnesium carbonate.

The body pigments of the present invention can be used in cosmetics, plastics, paints, coating media, powder coatings, agricultural foils, laser markings, prints, inks and resins, and paper etc., and also can be used as the flame retardant incorporated thereto.

Use for Cosmetics

The uses of the body pigments according to the present invention as a cosmetics product include make-up cosmetics, hair care products, and antiperspirants. For example, the body pigments can be used in-gel, lipstick, foundation (including emulsion, liquid, oil-type, etc.), compact cake, cream, lipstick, rouge, mascara, nail enamel, eyebrow pencil, eye shadow, eye liner, hair products, antiperspirant powder, antiperspirant spray, etc. The content of the body pigment may be 1 to 50% by weight in a cosmetic product. For example, 1 to 25 wt % for foundation, 1 to 40 wt % for eye shadow, 1 to 20 wt % for lipstick, and 0.1 to 10 wt % for nail enamel can be mentioned.

Thus, the examples include above described cosmetics which combine a body pigment of the present invention as the essential ingredient and at least one active ingredient selected from among skin protectants, colorants, other body pigments, anti-sunburn agents, antiperspirants, moisturizers, antimicrobial agents/microbicides, skin feeling improver, oils, and foam stabilizers.

The body pigments of the present invention may be used for cosmetic materials as processed, but they also may be surface treated (for example, water repellant finishing with silicon oil, silan coupling agent, hydrogenpolysiloxane, and fluorine compound).

The skin protectants used in the present invention, which are a composition to protect the surface roughening of the skin, include paraffin, ester, higher alcohol, fats and fatty oils such as glyceride, and polymer emulsions or suspensions of acryl, styrene, ether, ester, and silicone.

The colorant and other body pigments used in the present invention include water-insoluble pigments, oil-soluble dyes, vat dyes, and color lakes, and more specific examples are shown below. Those are, titanium dioxide, calcium carbonate, clay, talc, barium sulfate, white carbon, chromium oxide, zinc oxide, iron black, yellow iron oxide, red iron oxide, Prussian Blue, ultramarine blue, fluorescent pigments, soluble azo dyes, insoluble azo dyes, condensed type azo dyes, phthalocyanine pigments, condensed polycyclic pigments, composited oxide pigments, graphite, mica (e.g., muscovite, phlogopite, synthetic mica, fluorine tetra silicon mica, etc.), metal oxide coated mica (e.g., titanium oxide coated mica, titanium dioxide coated mica, (hydroxided) iron oxide coated mica, mica coated with iron oxides and titanium oxides, mica coated with lower ordered titanium oxides), metal oxide coated graphite (e.g., titanium dioxide coated graphite, etc.), thin platelet-like alumina, metal oxide coated thin-platelet like alumina (e.g., titanium dioxide coated thin-platelet like alumina, iron oxide coated thin platelet-like alumina, $Fe_2O_3$ coated thin-platelet like alumina, $Fe_3O_4$ coated thin-platelet like alumina, interference color metal oxide coated thin-platelet like alumina, etc.), MIO, sericite, magnesium carbonate, silica, zeolite, hydroxyapatite, chromium oxide, cobalt titanate, glass beads, nylon beads, silicone beads, etc.

Examples of organic pigments include red nos. 2, 3, 102, 104, 105, 1.06, 201, 202, 203, 204, 205, 206, 207, 208, 213, 214, 215, 218, 219, 220, 221, 223, 225, 226, 227, 228, 230-1, 230-2, 231, 232, 405; yellow nos. 4, 5, 201, 202-1, 202-2, 203, 204, 205, 401, 402, 403, 404, 405, 406, 407; green nos. 3, 201, 202, 204, 205, 401, 402; blue nos. 1, 2, 201, 202, 203, 204, 205, 403, 404; orange nos. 201, 203, 204, 205, 206, 207, 401, 402, 403; brown no. 201; violet nos. 201, 401; black no. 401. Examples of natural colors include salol yellow, carmine, β-carotin, hibiscus color, capsaicin, carminic acid, laccaic acid, gurcumin, riboflavin, shikonin, etc.

The anti-sunburn agents used in the present invention include organic compounds such as benzophenone compounds, dibenzoyl methane derivatives, and cinnamate derivatives, and inorganic compounds such as titanium oxide and zinc oxide.

Other antiperspirants used in the present invention include aluminum hydroxychloride, tannic acid, and zinc sulfate, and the pigments obtained by the present invention may be used either independently or combined with the foregoing antiperspirants.

The moisturizers used in the present invention include glycerin, glycol, sorbitol, polyols such as polyethylene glycol, etc.

The antimicrobial agents/microbicides used in the present invention include: alcohols such as ethyl alcohol and iso-propyl alcohol; phenols such as phenol and ortho-phenylphenol; aldehydes such as formaldehyde and glutaraldehyde; carboxylic acids such as benzoic acid (Na), 10-zinc undecylenate, and octanoic acid (salt); various thiazoles; various peroxides; and various quaternary amine surfactant.

The skin feeling improvers used in the present invention may be other body pigments or powders such as synthetic macromolecule particles and naturally occurring polymers. Examples include inorganic compounds such as talc, kaoline, sericite, calcium carbonate, magnesium silicate, and silicates; synthetic macromolecules such as nylon powder, polyethylene powder, polystyrene powder, tetron powder, epoxy resin powder, silicone resin; and naturally occurring polymers such as chitosan particle, starch particle, cellulose particle, silk powder, and crystalline cellulose powder.

The oils used in the present invention may be either volatile or nonvolatile oils, and examples include liquid oils such as: hydrocarbon oil (e.g., mineral oil), ester oil (e.g., isopropyl myristate, caprylic acid triglyceride, etc.), liquid oils such as vegetable oil, low-viscosity silicone oil, and volatile silicone oil; solid type paraffin and vaseline; ceramide, ethylene glycol fatty acid diester, dialkyl ether, etc.; compounds having silanol chain such as methylpolysiloxane, methylphenylsiloxane, and methylhydrogenpolysiloxane; silicone resin; and silicone beads, etc.

The foam stabilizers used in the present invention, which are surfactants to stabilize a foam membrane, include water-soluble polymers and hydrophilic solids. Water-soluble polymers include nonionic polymers such as methyl cellulose, hydroxypropyl cellulose, polyvinyl alcohol, polyacrylamide; anionic polymers such as sodium salt of xanthan gum and polyacrylic acid and sodium salt of carboxymethyl cellulose; and cationic polymers such as hydroxypropyl trimethylammonium chloride guar gum and hydroxypropyl trimethylammonium chloride starch. Perfumes are also appropriately used in the present invention. Also optionally used are surfactants such as various sodas, potash soap, various metal-containing (zinc, calcium, magnesium) soaps, and various sorbitan fatty acid esters.

Application for Resins

The flame retardant compositions incorporating the body pigments of the present invention as the essential component to resin component will be described below.

The body pigments of the present invention may be used for flame retardants by incorporating them into resins and paper. In the case of resins, the body pigments are either incorporated directly into the resins or premixed as a pellet and then further mixed with the resins, and thereafter the mixture can be formed into various molded products by extrusion, calendering, blowing, etc. The body pigments may be used as the resin composition for both thermoplastic resin of polyolefins, epoxies, polyesters, polyamides (nylons), polycarbonates, and polyacrylates and thermosetting resins. Also the body pigments of the present invention may be incorporated in the paper making process to obtain paper having a flame retardant property.

The entire disclosure of all applications, patents and publications, cited herein and of corresponding Japanese patent application No. 2002-065335, filed Mar. 11, 2002 is incorporated by reference herein.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Example 1

Two liter of deionized water was heated to 85° C. under stirring, and to which, 1480 g of aqueous solution of magnesium sulfate (0.45 mol/l, $MgSO_4.7H_2O$) was added while maintaining the solution at a pH of 9.0 by simultaneously adding an aqueous solution of 32 wt % sodium hydroxide. After adding these aqueous solutions, the suspension was filtered, washed with deionized water, and dried at 110° C. The obtained powder was observed on SEM photography to confirm that it consisted of substantially spherical particles, the individual particles having a structure in which leaf-shaped flakes are combined and/or intersected and a diameter of 8 to 17 μm. X-ray diffraction analysis also confirmed that the powder was $Mg(OH)_2$.

Example 2

Two liter of deionized water was heated to 75° C. under stirring, and to which, 1480 g of aqueous solution of magnesium sulfate (0.45 mol/l, $MgSO_4.7H_2O$) was added while maintaining the solution at a pH of 9.0 by simultaneously adding an aqueous solution of 32 wt % sodium hydroxide. After adding these aqueous solutions, the suspension was filtered, washed with deionized water, and dried at 110° C. The obtained powder was observed on SEM photography to confirm that it consisted of substantially spherical particles, the individual particles having a structure in which leaf-shaped flakes are combined and/or intersected, and a diameter of 7 to 10 μm. X-ray diffraction analysis also confirmed that the powder was $Mg(OH)_2$.

Example 3

Two liter of deionized water was heated to 85° C. under stirring, and to which, 1510 g of aqueous solution consisting of 1350 g of water, 28.4 g of sodium sulfate, and 150 g of magnesium sulfate ($MgSO_4.7H_2O$) was added while maintaining the solution at a pH of 9.0 by simultaneously adding an aqueous solution of 32 wt % sodium hydroxide. After adding these aqueous solutions, the suspension was filtered, washed with deionized water, and dried at 110° C. The obtained powder was observed on SEM photography to confirm that it consisted of substantially spherical particles, the individual having a structure in which leaf-shaped flakes are combined and/or intersected and a diameter of 5 to 30 μm. X-ray diffraction analysis also confirmed that the powder was $Mg(OH)_2$.

Example 4

Two liter of deionized water was heated to 80° C. under stirring, and to which, 1180 g of aqueous solution consisting of 1000 g of water, 30 g of potassium sulfate, 20 g of sodium sulfate, and 130 g of magnesium sulfate ($MgSO_4 \cdot 7H_2O$) was added while maintaining the solution at a pH of 9.0 by simultaneously adding an aqueous solution of 10 wt % sodium carbonate. After adding these aqueous solutions, the suspension was filtered, washed with deionized Water, and dried at 110° C. The obtained powder was observed on SEM photography to confirm that it consisted of substantially spherical particles having a structure in which leaf-shaped flakes being either combined or intersected and a diameter of 47 to 57 μm. X-ray diffraction analysis also confirmed that the powder was $Mg_5(CO_3)_4(OH)_2 \cdot 4H_2O$.

Comparative Sample 1

An aqueous solution of a temperature of 85° C. was prepared by dissolving 45 g of magnesium sulfate in 2000 g of deionized water under stirring, and thereafter, it was maintained at a pH of 9.7 by adding an aqueous solution of 10 wt % sodium carbonate. After adding the aqueous solution of sodium carbonate, the suspension was filtered, washed with deionized water, and dried at 110° C. Observation by SEM photography revealed that the obtained powder contained leaf-shaped particles but not combined and/or intersected into spherical particles.

Comparative Sample 2

An aqueous solution of a temperature of 85° C. was prepared by dissolving 50 g of magnesium sulfate in 2000 g of deionized water under stirring, and thereafter, it was maintained at a pH of 11.0 by adding an aqueous solution of 32 wt % sodium hydroxide. After adding the aqueous solution of sodium hydroxide, the suspension was filtered, washed with deionized water, and dried at 110° C. Observation by SEM photography revealed that the obtained powder contained leaf-shaped particles but not combined and/or intersected into spherical particles.

Test of Powder Physical Properties

As the index showing the skin feel such as spreadability, slipping property and adhesive property, a mean friction coefficient (MIU value) was measured by a KES-SE-DC tester manufactured by KATOTECH Co. Ltd. and a compression energy and compressive resiliency were measured by use of a KES-G5 compression tester manufactured by the same corporation.

1. Measurement of Friction Coefficient (MIU Value)

Measurement Method:

A powder specimen was adhered on one side surface of double-faced adhesive type of which other side surface was adhered on the glass slide and its mean friction coefficient was measured with a silicon sensor on the KES-SE-DC tester while sliding the specimen by 20 mm.

TABLE 1

Measured MIU values

| Specimen | Mean MIU values (MIU) |
| --- | --- |
| Example 1 | 0.35 |
| Example 2 | 0.41 |
| Example 3 | 0.31 |
| Example 4 | 0.32 |
| NylonPowder 12 | 0.49 |
| Biron ESQ | 0.55 |

The result shown in Table 1 revealed that the body pigments according to the present invention have lower MIU values thereby indicating better spreadability compared to nylon powder particles ('NylonPowder 12' from Toray) and bismuth oxychloride particles ('Biron ESQ' from MERCK) both of which have approximately the same particle size.

2. Measurement of Compression Energy and Compressive Resiliency

Measurement Method:

0.1 g of powder specimen was weighed and placed in a cylindrical case which was compacted by applying vibration thereon to reduce blank volume in the inter-powder. The cylindrical case was set on the KES-G5 compression tester for measurement. Five measurements were made to obtain evaluation data after excluding the first measurement from the evaluation data because of its large variation due to the blank volume remained in the powder. The results are shown below.

TABLE 2

Measured compression energy

| Specimen | Compression energy (gf · cm/cm$^2$) |
| --- | --- |
| Example 1 | 0.19 |
| Example 2 | 0.23 |
| Example 3 | 0.16 |
| Example 4 | 0.42 |
| NylonPowder 12 | 0.59 |
| Biron ESQ | 0.38 |

The result shown in Table 2 revealed that the body pigments according to the present invention have a compression energy of less than that of 'NylonPowder 12' and less than or nearly equal to that of 'Byron ESQ', that indicates their high crumbling property.

TABLE 3

Measured compressive resiliency

| Specimen | Compressive resiliency (%) |
| --- | --- |
| Example 1 | 16 |
| Example 2 | 21 |
| Example 3 | 19 |
| Example 4 | 31 |
| NylonPowder 12 | 44 |
| Biron ESQ | 39 |

Table 3 shows the comparison of the measurements of compressive resiliency. The body pigments obtained by the present invention have compressive resiliency of a little lower than that of the known nylon particle. These compression test results confirmed that the body pigments according to the present invention have spreadability on the skin as well as crumbling property thereby indicating good slipping property and adhesiveness.

3. Measurement of Oil Absorption

Measurement Method:

Oil absorption was measured by using linseed oil, lactic acid, and propionic acid as the oil component with a known method (measurement method for the standardization of cosmetics materials).

TABLE 4

Measured oil absorption

| oil component | Specimen | oil absorption (ml/100 g) |
| --- | --- | --- |
| Linseed oil | Example 1 | 50 |
|  | Example 2 | 110 |
|  | Example 3 | 95 |
|  | Example 4 | 310 |
|  | NylonPowder 12 | 65 |
|  | Biron ESQ | 45 |
| Lactic acid | Example 1 | 120 |
|  | Example 2 | 100 |
|  | Example 3 | 105 |
|  | Example 4 | 375 |
|  | NylonPowder 12 | 75 |
|  | Biron ESQ | 30 |
| Propionic acid | Example 1 | 60 |
|  | Example 2 | 75 |
|  | Example 3 | 80 |
|  | Example 4 | 345 |
|  | NylonPowder 12 | 80 |
|  | Biron ESQ | 40 |

The results shown in Table 4 revealed that the body pigments in the present invention consisting of magnesium hydroxide and magnesium carbonate have oil absorption more than or equal to that of the body pigments available on the market ('NylonPowder 12' and 'Biron ESQ') for lactic acid which is close to the sweat and the secreta of the sebaceous. The result also confirmed that compositions with a copious of basic magnesium carbonate component have especially large oil absorption, and are therefore suitable for use in antiperspirants. Furthermore, these results and SEM observation confirmed that the group using aqueous solution of magnesium formed by adding sodium sulfate to magnesium sulfate had larger porosities compared with the group of no sodium sulfate addition.

Each cosmetics composition was prepared by the following formulation.

Preparation Formulation Sample 1:

Use Example for Compact Powder:

| | |
|---|---|
| Talc | 50 parts |
| Pigments of example 3 | 50 parts |
| Colorant | 5 parts |
| Isopropyl myristate | a suitable amount |
| Magnesium stearate | 2 parts |

Use Example for the Foundation:

| | |
|---|---|
| Talc | 38 parts |
| Pigments of example 3 | 10 parts |
| Mica (8 µm) | 10 parts |
| Magnesium stearate | 3 parts |
| NylonPowder 12 | 8 parts |
| Yellow iron oxide | 1.9 parts |
| Red iron oxide | 0.8 parts |
| Titanium oxide | 1.0 parts |
| Mineral oil | a suitable amount |
| (Caprylic acid, capric acid) Triglycerid | 3.3 parts |
| Buthyl paraben | 0.1 parts |

The substantially spherical body pigments obtained by the present invention have an appropriate crumbling property and therefore exhibit a good slipping property on the skin. They also have good adhesiveness and large oil absorption, and therefore are suitable for cosmetics use. When the body pigment is dominantly composed of magnesium hydroxide, it is suitable for use in flame retardants since it has a substantially spherical massive structure in which leaf-shaped flakes are combined or intersected each other.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A body pigment comprising a metal-containing compound, wherein said body pigment has a structure in which more than two metal-containing compound flakes having different orientations are combined and/or intersected which pigment is prepared by a process comprising: simultaneously dropping an aqueous solution of metal-containing salt and an alkaline aqueous solution or an aqueous solution of carbonate salt into water while stirring to form a precipitate separating/washing said precipitate thereafter, and drying the same.

2. The body pigment according to claim 1, wherein said body pigment is of particles with an outer shape that is substantially spherical.

3. The body pigment according to claim 2, wherein said metal-containing compound is a magnesium compound.

4. The body pigment according to claim 1, wherein said metal-containing compound is a magnesium compound.

5. The body pigment according to claim 4, wherein said magnesium compound comprises one or more of magnesium hydroxide, basic magnesium carbonate, and magnesium oxide.

6. The body pigment according to claim 1, wherein the mean particle diameter of said body pigment is 3 to 80 µm.

7. The body pigment according to claim 1, wherein said metal-containing compound is either a metal-containing compound predominantly composed of magnesium hydroxide whose oil absorption is not more than 150 ml/100 g or a metal-containing compound predominantly composed of basic magnesium carbonate whose oil absorption is 150 to 400 ml/100 g.

8. The body pigment according to claim 1, wherein the friction coefficient, MIU value, of said body pigment, measured with a KES friction tester, is not larger than 0.6.

9. The body pigment according to claim 1, wherein the compression energy of said body pigment, measured with a KES compression tester, is 0.1 to 0.7 gf·cm/cm2.

10. The body pigment according to claim 1, wherein the compressive resiliency of said body pigment, measured with a ICES compression tester, is 15 to 50%.

11. A process for preparing a body pigment of claim 1, comprising:
simultaneously dropping an aqueous solution of metal-containing salt and
an alkaline aqueous solution or an aqueous solution of carbonate salt,
into water while stirring to form a precipitate, separating/washing said precipitate thereafter, and drying the same.

12. The process for preparing a body pigment according to claim 11, further comprising a calcuming step after the drying.

13. The process for preparing a body pigment according to claim 11, wherein said aqueous solution of metal-containing salt comprises sulfate ions and the ion concentration ratio of sulfate ion/metal ion is 0.3 to 2.0.

14. The process of claim 13, wherein metal-containing salt is magnesium sulfate.

15. The process of claim 11, wherein the aqueous solutions are simultaneously dropped into water preheated to above 50° C. under stirring while maintaining its pH at a constant value within a range of 7.5 to 11.

16. The process of claim 11, wherein the aqueous alkaline solution or aqueous solution of carbonate contains at least one of sodium hydroxide, potassium hydroxide, anunonium hydroxide, sodium carbonate, potassium carbonate, and ammonium carbonate.

17. A cosmetic material comprising the body pigment according to claim 1, wherein said cosmetic material further comprises one or more of a skin protectant, colorant, other body pigment, anti-sunburn agent, antiperspirant, moisturizer, antimicrobial agent/microbicide, skin feeling improver, and oil.

18. A makeup cosmetic material, comprising at least 5% by weight of the body pigment according to claim 1.

19. A flame retardant molded product, comprising resin or paper and the body pigment according to claim 1.

20. A plastic, paint, coating, powder coating, agricultural foil, laser markable plastic, or printing ink, comprising the body pigment of claim 1.

* * * * *

UNITED STATES PATENT AND TRADEMARK OFFICE
CERTIFICATE OF CORRECTION

PATENT NO.         : 7,018,464 B2                                            Page 1 of 1
APPLICATION NO. : 10/384781
DATED              : March 28, 2006
INVENTOR(S)        : Tamio Noguchi It is certified that error appears in the above-identified patent and that said Letters Patent is hereby corrected as shown below:

Column 14, line 22, reads "ICES" should read -- KES --
Column 14, line 33, reads "calcuming" should read -- calcining --
Column 14, line 47, reads "anunonium" should read -- ammonium --

Signed and Sealed this

Fourth Day of December, 2007

JON W. DUDAS
*Director of the United States Patent and Trademark Office*